United States Patent [19]

Haskell et al.

[11] 4,374,138

[45] Feb. 15, 1983

[54] ANTIBACTERIAL AMIDE COMPOUNDS, COMPOSITIONS, AND METHODS OF USE

[75] Inventors: Theodore H. Haskell, Ann Arbor; Marland P. Hutt, Saline, both of Mich.

[73] Assignee: Warner-Lambert Company, Morris Plains, N.J.

[21] Appl. No.: 321,020

[22] Filed: Nov. 13, 1981

[51] Int. Cl.$^3$ .................. A61K 31/47; C07D 499/70; C07D 215/22
[52] U.S. Cl. ................................ 424/258; 260/239.1; 546/156
[58] Field of Search ...................... 260/239.1; 424/258; 546/156

[56] References Cited

U.S. PATENT DOCUMENTS

| | | | |
|---|---|---|---|
| 4,241,062 | 12/1980 | Hannah | 260/239.1 |
| 4,263,302 | 4/1981 | Matsubara et al. | 260/239.1 |
| 4,273,932 | 6/1981 | Matsubara et al. | 260/239.1 |

*Primary Examiner*—Natalie Trousof
*Assistant Examiner*—Vera C. Clarke
*Attorney, Agent, or Firm*—Walter Patton

[57] ABSTRACT

Novel organic amide compounds which are N-[ureidodihydro-oxo-3-quinolinylcarbonyl]penicillin compounds having broad spectrum antibacterial utility are provided by (a) reacting the free amino acid of the appropriate penicillin or the acid salt or silylated derivative or complex thereof with a reactive derivative of the corresponding ureido-dihydro-oxo-3-quinolinecarboxylic acid or (b) reacting the free amino acid 6-aminopenicillanic acid or a related compound or the acid salt or silylated derivative thereof with a reactive derivative of the corresponding D-N-[ureidodihydro-oxo-3-quinolinylcarbonyl]-2-substituted glycine. Pharmaceutical compositions containing said compounds and methods for treating infections using said compositions are also disclosed.

10 Claims, No Drawings

ANTIBACTERIAL AMIDE COMPOUNDS, COMPOSITIONS, AND METHODS OF USE

SUMMARY AND DETAILED DESCRIPTION

The present invention relates to novel chemical compounds that are useful as pharmacological agents and to methods for their production. More particularly, the invention relates to novel organic amide compounds having the formula $$M-\overset{O}{\underset{\|}{C}}-NH-\underset{R_3}{CH}-\overset{O}{\underset{\|}{C}}-NH-\text{[β-lactam-S-C(CH}_3)_2\text{-CO}_2\text{H]}$$

and pharmaceutically acceptable salts thereof; wherein

M is $$R_1-NH-\overset{O}{\underset{\|}{C}}-NH-\text{[quinolin-2(1H)-one]}$$

A or $$R_1-NH-\overset{O}{\underset{\|}{C}}-NH-\text{[4-oxo-1,4-dihydroquinoline]}$$

B $R_1$ is lower alkyl or $$R_2-X-\overset{O}{\underset{\|}{C}}-\text{lower alkyl;}$$

$R_2$ is hydrogen or lower alkyl; X is O or NH and $R_3$ is phenyl, 4-hydroxyphenyl, 2-thienyl or cyclohexa-1,4-dien-1-yl.

The preferred compounds are those wherein M is A and the $$R_1-NH-\overset{O}{\underset{\|}{C}}-NH- \text{ group}$$

is in the 6-position.

Lower alkyl, where not specifically defined, is defined as a hydrocarbon fragment of from one to six carbon atoms.

In accordance with the invention the foregoing amide compounds having the formula $$M-\overset{O}{\underset{\|}{C}}-NH-\underset{R_3}{CH}-\overset{O}{\underset{\|}{C}}-NH-\text{[β-lactam]}$$

and pharmaceutically acceptable salts thereof wherein M and $R_3$ are as previously defined are produced by reacting a compound of the formula $$R_3-\underset{NH_2}{CH}-\overset{O}{\underset{\|}{C}}-NH-\text{[β-lactam]}$$

or the basic salt, silylated derivative (preferably the disilylated) or complex (preferably the dimethylsulfoxide) thereof with a reactive derivative of a substituted dihydro-oxo-quinolinecarboxylic acid compound having the formula $$M-CO_2H$$

wherein M and $R_3$ are as previously defined.

Some examples of reactive derivatives of the substituted-dihydro-oxo-quinolinecarboxylic acid compound suitable for the reactive are the acid halides (especially the acid chloride), the imidazolide, mixed anhydrides (especially those from an alkyl chloroformate such as methyl, ethyl, and isobutyl chloroformate or pivaloyl chloride), and activated esters such as the pentachlorophenyl ester and N-hydroxysuccinimide ester.

The reactants are normally employed in approximate equimolar quantities, although an excess of either (oxoquinolinecarboxylic acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin compounds in the free acid or salt form, aqueous solutions may be used for acylation with an acid halide or mixed anhydride under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of (substituted) dihydro-oxo-quinolinecarboxylic acid compounds which are required as starting materials in the foregoing process can be prepared according to any of a variety of methods.

A substituted-dihydro-oxo-quinolinecarboxylic acid may be converted to its acid chloride utilizing thionyl chloride, its mixed anhydride utilizing ethyl chloroformate, its pentachlorophenyl ester by esterification with pentachlorophenol and its imidazolide by reacting the acid with 1,1'-carbonyldiimidazole.

Compounds of the formula

M—CO₂H wherein M is as previously defined are prepared by reacting a compound of the formulae

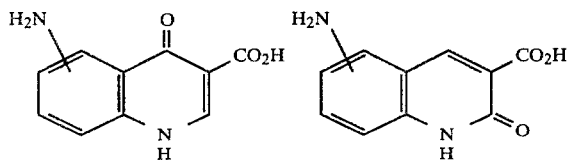

(known)

with a compound of the formula

R'—N=C=O wherein R' is as previously defined.

The compound of the formula

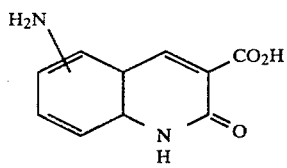

is prepared by hydrogenation of a compound of the formula

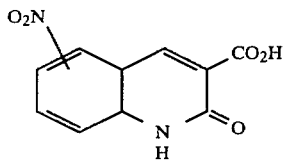

which is in turn prepared by nitration and deesterification of the known compound of the formula

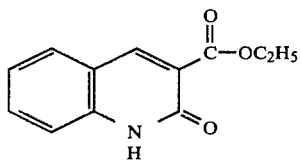

The silylated amino acid starting materials can be prepared by reacting an amino acid of the formula

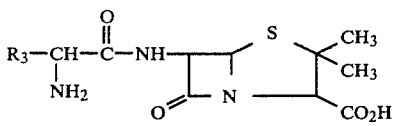

or a salt thereof wherein R₃ is as previously defined in anhydrous form with either one or two equivalents of a tri(lower alkyl)silyl chloride in the presence of triethylamine. The preferred silylating agents are trimethylsilyl chloride and dimethyl dichlorosilane. When two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

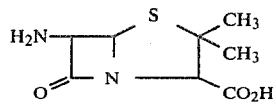

or the corresponding acid salt or silylated derivative thereof with a reactive derivative of D-N-[substituted-dihydro-oxo-quinolinylcarbonyl]-2-substituted glycine having the formula

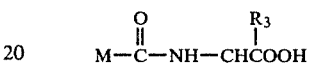

where R and R₃ have the aforementioned significance.

Some examples of reactive derivatives of the D-N-(dihydro-oxo-quinolinylcarbonyl)-2-substituted glycine compounds suitable for the reaction are the acid halides, mixed anhydrides (especially those formed from an alkyl chloroformate such as ethyl chloroformate and isobutyl chloroformate), and activated esters such as the pentachlorophenyl ester and N-hydroxysuccinimide ester. Since racemization is more likely with the acid halide, the other forms are generally preferred. The reactants are normally employed in approximate equimolar quantities, although an excess of either (quinolinylic acid compound or penicillanic acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 6-aminopenicillanic acid may be reacted with an acid chloride or mixed anhydride in the free acid or salt form using aqueous solutions under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of D-N-[substituted-dihydro-oxo-quinolinylcarbonyl]-2-substituted glycines which are required as starting materials in the foregoing process can be prepared by methods illustrated in greater detail hereinafter.

D-N-[substituted]-dihydro-oxo-quinolinylcarbonyl-2-substituted glycine compounds may be prepared by reacting the corresponding reactive derivative of 6-(substituted)-dihydro-oxo-quinolinecarboxylic acid, such as acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

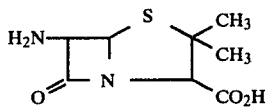

with a hexaalkyldisilazane. The preferred silylating agent is hexamethyldisilazane. Only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention.

The compounds of the invention can exist in anhydrous form, as well as in solvated, including hydrated, forms. In general, the hydrated forms and the solvated forms with pharmaceutically acceptable solvents are equivalent to the anhydrous or unsolvated forms for the purposes of the invention.

The oxo-quinoline segment of the compounds of this invention may be capable of undergoing keto-enol tautomerism to give hydroxyquinoline. Such a tautomer is equivalent to the oxo-quinoline (quinolone) for the purposes of the invention and are included within the above shown structures.

The compounds of the present invention can exist in various stereoisomeric forms. More specifically, the newly introduced amino acid fragments of the compounds may be in the form of the D-isomer, L-isomer or a mixture thereof [DL-mixture (partial or complete racemization)]. The invention is intended to include all of the isomeric forms and mixtures thereof.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds.

Thus, the compounds of this invention and their non-toxic pharmaceutically acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

ACTIVITY TABLE

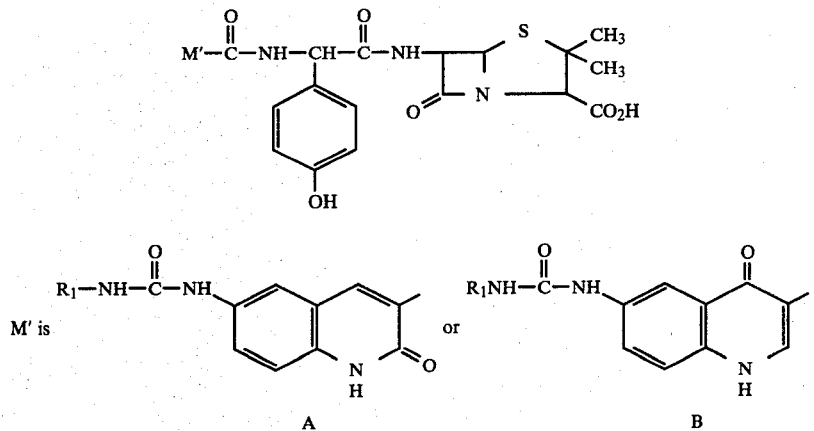

| | | Minimal Inhibitory Concentration (µg/ml) | | | | | | | | |
|---|---|---|---|---|---|---|---|---|---|---|
| | | Staph Aureus | Klebs. Pneu. | Serr. Mar. | Entero C. | Pseudo. Aeru | | E. Coli | | Prot. Vulg. |
| $M^1$ | $R_1$ | UC-76 | MGH-2 | IMM-16 | IMM-11 | 28 BRK | UI-18 | Brig | Vogel | 1810 |
| A | $CH_3CH_2$ | 0.4 | 6.3 | 6.3 | 3.1 | 0.4 | 1.6 | 1.6 | 3.1 | 1.6 | 1.6 |
| A | $C_2H_5OCCH_2$ (O=) | 1.6 | 12.5 | 12.5 | 12.5 | 3.1 | 3.1 | 3.1 | 12.5 | 6.3 | 6.3 |
| A | $C_2H_5NHCCH_2$ (O=) | 0.8 | 12.5 | 12.5 | 3.1 | 1.6 | 1.6 | 1.6 | 6.3 | 1.6 | 1.6 |

ACTIVITY TABLE-continued

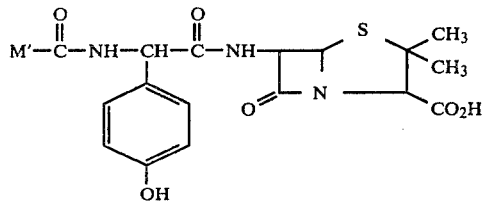

M' is 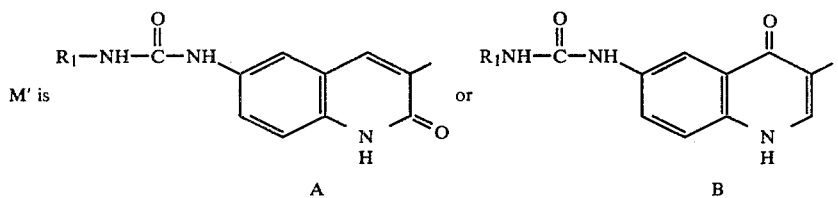

| | | Minimal Inhibitory Concentration (μg/ml) | | | | | | | | |
|---|---|---|---|---|---|---|---|---|---|---|
| | | Staph Aureus | Klebs. Pneu. | Serr. Mar. | Entero C. | Pseudo. Aeru | | E. Coli | | Prot. Vulg. |
| $M^1$ | $R_1$ | UC-76 | MGH-2 | IMM-16 | IMM-11 | 28 BRK | UI-18 | Brig | Vogel | 1810 |
| A | O‖H₂NCCH₂ | 0.8 | 12.5 | 12.5 | 6.3 | 0.8 | 0.8 | 1.6 | 6.3 1.6 | 1.6 |
| B | CH₃CH₂ | 0.8 | 3.1 | 1.6 | 3.1 | 0.8 | 0.4 | 3.1 | 6.3 0.4 | 0.8 |

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg to about 1000 mg of active compound per unit dose form.

The invention is illustrated by the following examples.

STARTING MATERIALS

A. 1,2-Dihydro-6-nitro-2-oxo-3-quinolinecarboxylic acid

A solution of 10.0 g (46 mmol) of 1,2-dihydro-2-oxo-3-quinolinecarboxylic acid, ethyl ester [J. Chem. Soc., 2518 (1962)] and 50 ml of sulfuric acid is stirred in an ice bath and a cold mixture of 9.75 ml of 70% nitric acid and 9.75 ml of sulfuric acid is added dropwise over 10 minutes. The reaction solution is stirred with ice bath cooling for 1 hour and then is poured into ice and water with stirring. The resulting solid is collected by filtration and washed with water and ethanol. After drying, 10.7 g of the requisite ester is obtained, mp>310°. The structure is assigned by an unequivocal synthesis from the condensation of 2-amino-5-nitrobenzaldehyde and diethyl malonate to give the same 1,2-dihydro-6-nitro-2-oxo-3-quinolinecarboxylic acid, ethyl ester.

A mixture of 9.7 g (37 mmol) of the above ester and 200 ml of 1 N sodium hydroxide is heated on the steam bath for 1¼ hours. The resulting suspension is poured over ice and acidified with 250 ml of 1 N hydrochloric acid. The solid is collected by filtration and washed with water and ethanol to give 8.15 g of the title acid, mp>310°.

B. 6-Amino-1,2-dihydro-2-oxo-3-quinolinecarboxylic acid

A solution of 3.63 g (14.9 mmol) of 1,2-dihydro-6-nitro-2-oxo-3-quinolinecarboxylic acid and 200 ml of dimethylformamide is hydrogenated using 1 g of Raney nickel catalyst at 52 psi and 23° until the required amount of hydrogen uptake is obtained. The catalyst is filtered off and the filtrate is evaporated to dryness. The residue is treated with ethanol and 3.0 g of the desired product is filtered.

| UV (pH 7) | λ367 nm | $a_1^1$ | 257 |
|---|---|---|---|
| | 243 | | 1410 |

C. 8-Amino-1,4-dihydro-4-oxo-3-quinolinecarboxylic acid

A solution of 15.0 g (64 mmol) of 1,4-dihydro-8-nitro-4-oxo-3-quinolinecarboxylic acid [J. Amer. Chem. Soc., 68, 1264 (1946)] in 300 ml of dimethylformamide is hydrogenated using 1 g of Raney nickel catalyst at 51 psi and 23° until the required amount of hydrogen uptake is obtained. The catalyst is filtered off and the filtrate is concentrated to 50 ml and ethanol is added. The solid is collected by filtration and washed with ethanol and ether to give 9.7 g of the title compound.

| UV (pH 7) | λ327 nm | $a_1^1$ | 362 |
|---|---|---|---|
| | 238 | | 1370 |

EXAMPLE 1

N-[6-[[[(2-Ethoxy-2-oxoethyl)amino]carbonyl]amino]-1,2-dihydro-2-oxo-quinolinylcarbonyl]amoxicillin A mixture of 6.13 g (30 mmol) of 6-amino-1,2-dihydro-2-oxo-3-quinolinecarboxylic acid, 5.8 g (45 mmol) of ethyl isocyanatoacetate, 4.2 ml (30 mmol) triethylamine, and 60 ml of dimethylformamide is stirred at room temperature for 3 hours. The solution is evaporated to dryness, and the residue is treated with 1 N hydrochloric acid to give 9.23 g of 6-[[[(2-ethoxy-2-oxyethyl)amino]carbonyl]amino]-1,2-dihydro-2-oxo-3-quinolinecarboxylic acid, mp 285°–295° dec.

A mixture of 3.33 g (10.0 mmol) of the above quinoline acid, 3.24 g (20 mmol) of carbonyldiimidazole, and 45 ml of dimethylformamide is stirred at 50° to 53° for 30 minutes and at room temperature overnight. The solution is diluted with 150 ml of acetonitrile, and the solid is filtered to give 3.41 g of 6-[[(2-ethoxy-2-oxyethyl)amino]carbonyl]-1,2-dihydro-2-oxo-3-quinolinecarboxylic acid imidazolide.

A mixture of 1.92 g (5.0 mmol) of the above imidazolide, 3.17 g (5.0 mmol) of amoxicillin, 0.70 ml (5.0 mmol) of triethylamine, and 30 ml of N,N-dimethylacetamide is stirred for 15 minutes with cooling and for 4½ hours at room temperature. The solution is cooled and 1.56 ml (5.0 mmol) of 3.2 N sodium-2-ethylhexanoate in N,N-dimethylacetamide is added, and the solution is poured into 300 ml of ethyl acetate. The solid is filtered and added to 300 ml of ice and water and acidified to pH2 with 1 N hydrochloric acid. The mixture is centrifuged and the water is poured off. The wet solid is suspended in 250 ml of water and 1 N sodium hydroxide is added to pH7.0. The solution is filtered and lyophilized to give 3.4 g of the title compound as the sodium salt.

| UV (pH 7) | λ368 nm | $a_1^1$ 68 | $[\alpha]^{23}$ + 109° (cl, pH 7) |
|---|---|---|---|
| | 293 | 185 | |
| | 250 | 516 | |

EXAMPLE 2

N-[6-[[[[2-(Ethylamino)-2-oxoethyl]amino]carbonyl]amino]-1,2-dihydro-2-oxo-3-quinolinylcarbonyl]amoxicillin A mixture of 3.00 g (9.0 mmol) of 6-[[[(2-ethoxy-2-oxyethyl)amino]carbonyl]amino]-1,2-dihydro-2-oxo-3-quinolinecarboxylic acid, 10 ml of ethylamine and 30 ml of dimethylformamide is stirred at room temperature for 17 hours. The mixture is evaporated to dryness, and the residue is treated with 1 N hydrochloric acid. The solid is filtered to give 2.8 g of 6-[[[[2-(ethylamino)-2-oxoethyl]amino]carbonyl]amino]-1,2-dihydro-2-oxo-3-quinolinecarboxylic acid, mp 265°–7° dec.

A mixture of 2.49 g (7.5 mmol) of the above quinoline acid, 2.43 g (15.0 mmol) of carbonyldiimidazole, and 40 ml of dimethylformamide is heated at 50° to 52° for 30 minutes and is stirred for 3¾ hours at room temperature. The solution is diluted with 150 ml acetonitrile and stirred for 15 minutes. The solid is filtered to give 2.82 g of 6-[[[[2-(ethylamino)-2-oxo-ethyl]amino]carbonyl]amino]-1,2-dihydro-2-oxo-3-quinolinecarboxylic acid imidazolide.

A mixture of 2.80 g (7.32 mmol) of the above imidazolide, 4.64 g (7.32 mmol) of amoxicillin, 1.02 g (7.32 mmol) of triethylamine, and 80 ml of N,N-dimethylacetamide is stirred with cooling for 15 minutes and at room temperature for 5 hours. The reaction mixture is filtered using Celite and 2.3 ml (7.3 mmol) of sodium 2-ethylhexanoate in N,N-dimethylacetamide is added. The solution is poured into 350 ml of ethyl acetate, and the solid is filtered. The solid is dissolved with 300 ml of ice and water and acidified to pH2 with 1 N hydrochloric acid. The mixture is centrifuged and the water poured off. The wet solid is suspended in 300 ml of water and 1 N sodium hydroxide is added to pH7.0. The solution is filtered and lyophilized twice to give 4.08 g of the title compound as the sodium salt.

| UV (pH 7) | λ372 nm | $a_1^1$ 70 | $[\alpha]^{23}$ + 130° (cl, pH 7) |
|---|---|---|---|
| | 294 | 184 | |
| | 252 | 550 | |

EXAMPLE 3

N[-6-[[[(2-Amino-2-oxoethylamino)carbonyl]amino]-1,2-dihydro-2-oxo-3-quinolinylcarbonyl]amoxicillin A mixture of 2.62 g (7.86 mmol) of 6-[[[(2-ethoxy-2-oxyethyl)amino]carbonyl]amino]-1,2-dihydro-2-oxo-3-quinolinecarboxylic acid and 100 ml of methanol saturated with ammonia is stirred with cooling for 3 hours and at room temperature overnight. The solid is filtered and treated with 1 N hydrochloric acid to give 2.10 g of 6-[[[(2-amino-2-oxyethyl)amino]carbonyl]amino]-1,2-dihydro-2-oxo-3-quinolinecarboxylic acid.

A mixture of 2.08 g (6.8 mmol) of the above quinoline carboxylic acid, 2.21 g (13.6 ml) carbonyldiimidazole, and 50 ml of dimethylformamide is heated at 53° to 56° for 55 minutes and is stirred overnight at room temperature. The mixture is diluted with 120 ml of acetonitrile and is filtered to give 2.30 g of 6-[[[(2-amino-2-oxyethyl)amino]carbonyl]amino]-1,2-dihydro-2-oxo-3-quinolinecarboxylic acid imidazolide.

A mixture of 2.26 g (6.38 mmol) of the above imidazolide, 4.04 g (6.38 mmol) of amoxicillin, 0.89 ml (6.38 mmol) of triethylamine, and 100 ml of N,N-dimethylacetamide is stirred with cooling for 5 minutes and at room temperature for 6 hours. The solution is cooled and 2.0 ml (6.4 mmol) of 3.2 N sodium 2-ethylhexanoate in N,N-dimethylacetamide is added. The solution is poured into 500 ml of ethyl acetate and the solid is filtered. The solid is dissolved with 200 ml of water, filtered and acidified to pH 1.5 with 1 N hydrochloric acid. The mixture is centrifuged and the water is poured off. The wet solid is suspended in water and 1 N sodium hydroxide is added to pH 6.5. The solution is filtered and lyophilized to give 4.05 g of the title compound as the sodium salt.

| UV (pH 7) | λ373 nm | $a_1^1$ 70 | $[\alpha]^{23}$ + 113° (cl, pH 7) |
|---|---|---|---|
| | 293 | 190 | |
| | 252 | 540 | |

EXAMPLE 4

N-[6-[[(Ethylamino)carbonyl]amino]-1,2-dihydro-2-oxo-3-quinolinylcarbonyl]amoxicillin A mixture of 4.08 g (20 mmol) of 6-amino-1,2-dihydro-2-oxo-3-quinolinecarboxylic acid, 2.37 ml (30 mmol) of ethyl isocyanate, 2.8 ml (20 mmol) of triethylamine and 50 ml of dimethylformamide is stirred with ice bath cooling for 4.5 hrs. The reaction solution is evaporated to dryness and is treated with 1 N hydrochloric acid and ethanol to yield 5.12 g of 6-[[(ethylamino)carbonyl]amino]-1,2-dihydro-2-oxo-3-quinolinecarboxylic acid.

A mixture of 5.07 g (18.4 mmol) of the above quinolinecarboxylic acid, 5.97 g (36.8 mmol) carbonyldiimidazole, and 70 ml dimethylformamide is heated at 48° to 49° for 45 minutes and is stirred at room temperature overnight. The mixture is diluted with 150 ml of acetonitrile and filtered to yield 5.73 g of 6-[[(ethylamino)carbonyl]amino]-1,2-dihydro-2-oxo-3-quinolinecarboxylic acid imidazolide.

A mixture of 1.97 g (6.00 mmol) of the above imidazolide, 3.80 g (6.00 mmol) of amoxicillin; 0.84 ml (6.00 mmol) of triethylamine, and 40 ml of N,N-dimethylacetamide is stirred with cooling for 15 minutes and at room temperature for 4 hours 15 minutes. The solution is cooled and 1.88 ml (6.0 mmol) of sodium-2-ethylhexanoate in N,N-dimethylacetamide is added and the solution is poured into 250 ml of ethyl acetate. The solid is filtered and washed with ethyl acetate and ether. The solid is dissolved with 200 ml of water and ice and is acidified to pH2 with 1 N hydrochloric acid. The solid is filtered and suspended in 200 ml of water. The pH is adjusted to 6.5 with 1 N sodium hydroxide and is filtered and lyophilized to yield 3.8 g of the title compound as the sodium salt.

| UV (pH 7) | λ372 nm | $a_1^1$ 198 | $[\alpha]^{23}$ + 162° (cl, pH 7) |
|---|---|---|---|
| | 294 | 217 | |
| | 252 | 560 | |

EXAMPLE 5

N-[6-[[(Ethylamino)carbonyl]amino]-1,4-dihydro-4-oxo-3-quinolinylcarbonyl]amoxicillin A mixture of 4.08 g (20 mmol) of 6-amino-1,4-dihydro-4-oxo-3-quinolinecarboxylic acid [J. Pharm. Sci., 11, 1051 (1963)] 2.37 ml (30 mmol) of ethyl isocyanate, 2.8 ml (20 mmol) of triethylamine and 50 ml of dimethylformamide is stirred at room temperature overnight. The solution is evaporated to dryness and the residue is treated with 1 N hydrochloric acid. The solid is filtered to give 4.56 g of 6-[[(ethylamino)carbonyl]-amino]-1,4-dihydro-4-oxo-3-quinolinecarboxylic acid, mp>320° C.

A mixture of 4.50 g (16.3 mmol) of the above quinoline acid, 5.30 g (32.7 mmol) carbonyldiimidzole, and 50 ml dimethylformamide is heated at 49°–56° for 50 minutes and is stirred at room temperature overnight. The reaction mixture is diluted with acetonitrile and 5.17 g of 6-[[(ethylamino)carbonyl]amino]-1,4-dihydro-4-oxo-3-quinolinecarboxylic acid imidazolide is filtered.

A mixture of 1.95 g (6.0 mmol) of the above imidazolide, 4.14 g (6.0 mmol) of amoxicillin; 0.84 ml (6.0 mmol) of triethylamine, and 40 ml of N,N-dimethylacetamide is stirred with cooling for 15 minutes and at room temperature for 2⅔ hours. The solution is poured into 250 ml of ice and water and is acidified to pH2 with 1 N hydrochloric acid. The solid is filtered, suspended in water and is filtered. The solid is suspended in 100 ml of water and 1 N sodium hydroxide added to pH6.5. The solution is filtered and lyophilized to give 3.1 g of the title compound as the sodium salt.

| UV (pH 7) | λ315 nm | $a_1^1$ 198 | $[\alpha]^{23}$ + 162° (cl, pH 7) |
|---|---|---|---|
| | 267 | 455 | |
| | 260 | 450 | |
| | 231 | 550 | |

We claim:

1. A compound of the formula

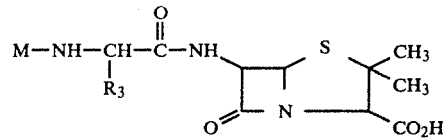

and pharmaceutically acceptable salts thereof; wherein M is

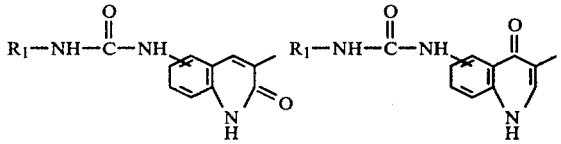

$R_1$ is lower alkyl or

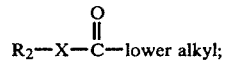

$R_2$ is hydrogen or lower alkyl; X is O or NH and $R_3$ is phenyl, 4-hydroxyphenyl, 2-thienyl or cyclohexa-1,4-dien-1-yl.

2. The compounds of claim 1 wherein M is

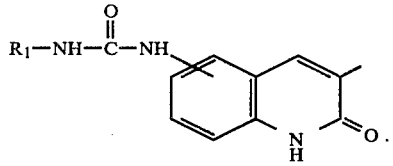

3. The compounds of claim 2 wherein

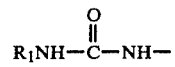

is in the 6-position.

4. The compound having the name N-[6-[[[(2-ethoxy-2-oxoethyl)amino]carbonyl]amino]-1,2-dihydro-2-oxoquinolinylcarbonyl]amoxicillin and pharmaceutically acceptable salts thereof.

5. The compound having the name N-[6-[[[[2-(ethylamino)-2-oxoethyl]amino]carbonyl]amino]-1,2-dihydro-2-oxo-3-quinolinylcarbonyl]amoxicillin and pharmaceutically acceptable salts thereof.

6. The compound having the name N-[-6-[[(2-amino-2-oxoethylamino)carbonyl]amino]-1,2-dihydro-2-oxo-3-quinolinylcarbonyl]amoxicillin and pharmaceutically acceptable salts thereof.

7. The compound having the name N-[6-[[(ethyl amino)carbonyl]amino]-1,4-dihydro-4-oxo-3-quinolylcarbonyl]amoxicillin and pharmaceutically acceptable salts thereof.

8. An antibacterial pharmaceutical composition comprising an antibactercally effective amount of a compound of claim 1 and a pharmaceutical carrier.

9. A method for treating bacterial infections in a mammal in need thereof which comprises administering thereto the pharmaceutical composition of claim 8.

10. A compound of the formula

M—Co₂H where M is as defined in claim 1 and salts thereof.

* * * * *